United States Patent
Herr et al.

(10) Patent No.: US 7,947,026 B2
(45) Date of Patent: May 24, 2011

(54) GLANS COMPATIBLE SINGLE UNIT SEMEN COLLECTION AND STORAGE DEVICE, KIT AND RELATED METHODS OF USE

(75) Inventors: John C. Herr, Charlottesville, VA (US); Arabinda Mandal, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 368 days.

(21) Appl. No.: 10/577,983

(22) PCT Filed: Nov. 5, 2004

(86) PCT No.: PCT/US2004/036916
§ 371 (c)(1),
(2), (4) Date: May 2, 2006

(87) PCT Pub. No.: WO2005/046560
PCT Pub. Date: May 26, 2005

(65) Prior Publication Data
US 2007/0031895 A1 Feb. 8, 2007

Related U.S. Application Data

(60) Provisional application No. 60/517,854, filed on Nov. 6, 2003, provisional application No. 60/684,601, filed on May 25, 2005.

(51) Int. Cl.
*A61F 5/44* (2006.01)
(52) U.S. Cl. ......... 604/349; 604/317; 604/322; 604/327
(58) Field of Classification Search .................. 604/317
See application file for complete search history.

(56) References Cited

U.S. PATENT DOCUMENTS

| | | | |
|---|---|---|---|
| 3,401,696 A | | 9/1968 | O'Brien |
| 4,690,678 A | | 9/1987 | Douglas-Hamilton |
| 5,055,411 A | | 10/1991 | Ericcson |
| 5,068,089 A | * | 11/1991 | Ericsson et al. ............... 422/61 |
| 5,244,453 A | | 9/1993 | Osbon |
| 5,501,650 A | | 3/1996 | Gellert |
| 5,569,225 A | * | 10/1996 | Fleury ........................... 604/323 |
| 5,605,803 A | | 2/1997 | Herr |

(Continued)

OTHER PUBLICATIONS

Marmar, J.L., Praiss, D.E. and Debenedictis, T.J., "Statistical Comparison of the Parameters of Semen Analysis of Whole Semen Versus the Fractions of the Split Ejaculate," Fertility & Sterility, 30(4):439-443, Oct. 1978.

Adoni, A. and Palti, Z., "Better Postcoital Test for Oligospermic Patients Using Split Ejaculate Artificial Insemination," Fertility & Sterility, 31(5):587-588, May 1979.

Propping, D., Katzorke, T. and Tauber, P.F., "Further Evaluation of the Split Ejaculate for Artificial Insemination," European J. of Obstetrics, Gynecology & Reproductive Biology, 11(6):385-394, May 1981.

(Continued)

*Primary Examiner* — Melanie J Hand
(74) *Attorney, Agent, or Firm* — Robert J. Decker

(57) ABSTRACT

A method and device to conform with the glans penis to recover ejaculated semen completely, to prevent the loss of initial sperm rich epididymal fractions, to avoid the use of a condom for masturbation, to eliminate the multi-step transfers of semen following ejaculation that are common with current methods, and to provide a single device that contains a semen collecting chamber that fits onto a glans penis. The device provides a storage and measuring reservoir, an optional cap, and a vertical stand in one integrally formed module in a sterile pack. The device and method will have multiple uses in a variety of contexts including, but not limited thereto: in the diagnosis of infertility, in semen donation, in vitro fertilization (IVF)/intra-cytoplasmic sperm injection (ICSI) clinics, hospitals, forensic laboratories and research laboratories and will be included in kits intended for over-the-counter sperm testing devices.

56 Claims, 12 Drawing Sheets

U.S. PATENT DOCUMENTS

| | | | |
|---|---|---|---|
| 5,961,503 A * | 10/1999 | Simmet et al. | 604/349 |
| 6,113,532 A * | 9/2000 | Yap | 600/38 |
| 6,129,214 A * | 10/2000 | Bar-Ami et al. | 209/235 |
| 6,149,580 A | 11/2000 | Dabney | |
| 6,493,884 B1 | 12/2002 | Muller | |
| 6,699,226 B2 * | 3/2004 | Velazquez | 604/349 |
| 6,864,046 B1 * | 3/2005 | Prien et al. | 435/2 |
| 2001/0044087 A1 | 11/2001 | Kontos | |
| 2003/0148365 A1 | 8/2003 | Morgan | |

OTHER PUBLICATIONS

Schill, W.B. and Littich, M., "Split Ejaculate Insemination With and Without the Addition of Kallikrein," Andrologia, 13(2):121-126, Mar.-Apr. 1981.

Sokol, R.Z., Madding, C.I., Handelsman, D.J. and Swerdloff, R.S., "The Split Ejaculate: Assessment of Fertility Potential Using Two in Vitro Test Systmes," Andrologia, 18(4):380-386, Jul.-Aug. 1986.

* cited by examiner

GLANS COMPATIBLE SINGLE UNIT SEMEN COLLECTION AND STORAGE DEVICE, KIT AND RELATED METHODS OF USE

CROSS-REFERENCE TO RELATED APPLICATIONS

This application is a national stage filing of International Application No. PCT/US2004/036916, filed on Nov. 5, 2004, which claims benefit of priority under 35 U.S.C. Section 119(e) from U.S. Provisional Application Ser. No. 60/517, 854, filed Nov. 6, 2003, entitled "Spermcollect: A Glans Compatible Single Unit Semen Collection and Storage Device, Kit, and Related Method thereof," the entire disclosures of which are hereby incorporated by reference herein in their entirety.

This application claims benefit of priority under 35 U.S.C. Section 119(e) from U.S. Provisional Application Ser. No. 60/684,601, filed May 25, 2005, entitled "Glans Compatible Single Unit Semen Collection and Storage Device, Kit, and Related Method thereof," the entire disclosure of which is hereby incorporated by reference herein in its entirety.

GOVERNMENT SUPPORT

This invention was made with government support under the Grant No. NIH-SBIR 116743 GI 11037 101 40410. The government has certain rights in the invention.

BACKGROUND OF THE INVENTION

Semen is comprised of sperm suspended in a fluid phase called seminal plasma. Semen analysis is the major step to determine the fertility status of a male patient or a sperm donor and involves counting spermatozoa with a microscope and examining their motility and morphology. Semen analyses are usually performed on ejaculates collected in a condom during coitus or by masturbation into a tube, bottle, or onto a plate. Freshly ejaculated human semen is a heterogeneous mixture consisting principally of fluids from prostate (approximately 20-30%), epididymis (approximately 10-15%), as well as the seminal vesicles (approximately 60-75%). The epididymal fraction contains the sperm. The seminal vesicles secrete a fluid that forms a soft coagulum in which spermatozoa are entrapped. Following ejaculation this clot undergoes liquefaction over a time course of approximately 20 minutes at approximately room temperature by the action of PSA (P30), a proteolytic enzyme originating in the prostate gland.

Collection and donation of semen is achieved by a variety of methods, each of which may have some drawbacks. Semen collection by masturbation using a condom is considered by some donors to be unesthetic or difficult. In other instances coitus with a partner might not be an option for semen collection. Furthermore, recovery of semen from a condom following ejaculation is always incomplete due to loss of unliquefied semen over the skin of penis as well as on the inner wall of the condom. The lack of complete recovery by this procedure may result in inconsistent semen evaluation. On the other hand semen collection by masturbation without condom directly into a tube, bottle or in a container may result in loss of sperm rich fractions primarily because human semen is ejaculated in split fractions associated with the orgasmic contractions. The initial portion of the ejaculate contains the sperm rich fraction originating in the epididymis along with secretions from Cowper's gland and prostate, followed by a mixture of prostatic and seminal vesicle secretions and finally the ejaculation wave culminates with the seminal vesicular coagulum. See Marmar, J. L., Praiss, D. E. and Debenedictis, T. J., "Statistical Comparison of the Parameters of Semen Analysis of Whole Semen Versus the Fractions of the Split Ejaculate," *Fertility & Sterility,* 30(4):439-443, 1978 October, of which is hereby incorporated by reference herein in its entirety. See Adoni, A. and Palti, Z., "Better Postcoital Test for Oligospermic Patients Using Split Ejaculate Artificial Insemination," *Fertility & Sterility,* 31(5):587-588, 1979 May, of which is hereby incorporated by reference herein in its entirety. See Propping, D., Katzorke, T. and Tauber, P. F., "Further Evaluation of the Split Ejaculate for Artificial Insemination," *European J. of Obstetrics, Gynecology & Reproductive Biology,* 11(6):385-394, 1981 May, of which is hereby incorporated by reference herein in its entirety. See Schill, W. B. and Littich, M., "Split Ejaculate Insemination With and Without the Addition of Kallikrein," *Andrologia,* 13(2):121-126, 1981 March-April, of which is hereby incorporated by reference herein in its entirety. See Sokol, R. Z., Madding, C. I., Handelsman, D. J. and Swerdloff, R. S., "The Split Ejaculate: Assessment of Fertility Potential Using Two in Vitro Test Systems," *Andrologia,* 18(4):380-386, 1986 July-August, of which is hereby incorporated by reference herein in its entirety.

Some of the embodiments of the present invention provide, among other things, a method and device to recover ejaculated semen completely, to prevent the loss of initial sperm rich epididymal fractions, to avoid the use of a condom for masturbation, to eliminate the multi-step transfers of semen following ejaculation that are common with current methods, and to provide a single device that contains a collecting chamber, a storage and measuring reservoir, and a vertical stand in one preformed module. The various embodiments of the present invention semen collection system and method will have multiple uses in a variety of contexts including, but not limited thereto: in the diagnosis of infertility, in semen donation, artificial insemination, in vitro fertilization (IVF)/intracytoplasmic sperm injection (ICSI) clinics, hospitals and laboratories and will be included in kits intended for over-the-counter sperm testing devices such as SPERMCHECK.

BRIEF SUMMARY OF INVENTION

Some advantages of at least some of the embodiments of the present invention are, among other things, to provide a semen collection device which will eliminate the loss of sperm rich initial fractions produced during ejaculation by masturbation, to eliminate the use of the condom during masturbation, to minimize multiple transfer steps related to sample loss, to obtain all semen fractions for analyses following liquefaction of the semen within a single unit and to provide a user friendly, cost effective unit to accompany sperm kits intended for home testing. The same device can also be used in conjunction with a condom to collect a postcoital sample from a condom into the present invention device following liquefaction. It may be noted that some embodiments of the present invention device may be commercialized as the SPERMCOLLECT collecting device, by ContraVac Incorporated.

At least one embodiment of the present invention method provides the collection of the sample by masturbation (or other stimulation) to avoid sample loss and complete recovery following ejaculation. It should be appreciated that sperm are present mainly in the initial fractions of the ejaculate. An initial step includes placing the glans accommodating portion of an embodiment of the present invention collection device over the glans penis of the erect penis before ejaculation begins to collect all fluids. Next the orifice of the urethra is placed into or aligned with the proximal end of the chamber tube before ejaculation. For instance, the urethra is optimally aligned with the desired/required location of the glans accommodating portion of the device and/or optimally aligned with the desired/required location of the reservoir of the device. The male human individual ejaculates directly in the proximal end of the chamber while the chamber is held tight against the glans. This step eliminates or virtually eliminates any loss of sperm rich fractions during early and late phases of ejaculation. The protruding member (e.g., legs or collar) adjacent to at least part of the chamber of the collection device, or any part of the chamber (e.g., glans accommodating portion, reservoir and/or adapter section), may incorporate a grip to facilitate tight apposition or fit of the glans penis to the glans accommodating portion of the collection device. Preferably, the chamber is kept over the glans penis until the completion of ejaculation and retraction of the penis to collect any seminal secretions at late stages of ejaculation. The chamber is allowed to stand (e.g., at room temperature or at desired temperature(s)) for spontaneous liquefaction of the semen sample for a desired or required durations (e.g., about 20 minutes or other selected period). After liquefaction or when desired additional steps or treatment may be taken. For instance, the collected sample can be mixed thoroughly by stirring with the supplied dropper or other tool or instrument. The thoroughly mixed semen sample is now ready for the examination/analysis of sperm count, morphology, motility, viability and markers of accessory sex gland secretion. In other embodiments of the present invention, if the semen is first collected in a condom, then the condom should be carefully removed following ejaculation after regression of the penis. The condom tip or other section can be cut or pierced and the condom can be left in the glans accommodating portion to recover the semen as it liquefies. After a period of time the mixing steps or other treatment steps may be applied.

Some aspects of some embodiments provides for a method and device that recovers ejaculated semen completely, prevents the loss of initial sperm rich epididymal fractions, avoids the use of a condom for masturbation, eliminates the multi-step transfers of semen following ejaculation that are common with current methods, and provides a single device that contains a semen collecting chamber that fits onto a glans penis. The device provides a storage and measuring reservoir, an optional cap, and a vertical stand in one preformed integrally formed module collecting device that may be provided in a sterile pack. The device and method will have multiple uses in a variety of contexts including, but not limited thereto: in the diagnosis of infertility, in semen donation, in vitro fertilization (IVF)/intra-cytoplasmic sperm injection (ICSI) clinics, hospitals, forensic laboratories and research laboratories and will be included in kits intended for over-the-counter sperm testing devices.

An aspect of an embodiment of the present invention provides a device for collecting semen received from a glans penis of a male human individual. The device comprising: a chamber comprising a distal end, a proximal end, and a conduit extending between the distal end and proximal end. The proximal end having a rim defining an aperture. The distal end having a surface that encloses the conduit. At least a portion of the conduit proximal to the proximal end having a tapered shape radially inward defusing a tapered section, whereby the tapered section accommodates the head of the glans penis. At least a portion of the conduit proximal to the distal end adapted for receiving the semen ejaculated from the glans penis, whereby the receiving portion provides a reservoir section for the semen.

An aspect of an embodiment of the present invention provides a test kit for analyzing the semen collected. The kit comprising: a surface on which the semen sample collected in the device can be deposited; and a means for analyzing the semen sample deposited on the surface.

An aspect of an embodiment of the present invention provides a test kit for analyzing the semen collected in the device whereby the reservoir section at least partially comprises at least one communication channel and the semen sample collected in the device can be received. The kit further comprises a means for analyzing the semen sample received from the communication channel.

An aspect of an embodiment of the present invention provides a test kit for analyzing the semen collected in a collecting device having a port thereon. The test kit includes: at least one communication channel in communication with the port, wherein semen sample collected in the device can be received via the port; and a means for analyzing the semen sample received from the communication channel.

An aspect of an embodiment of the present invention provides a method for collecting semen received from a glans penis of a male human individual during ejaculation. The method comprising: placing a semen collecting device in contact with the glans head of the individual; and receiving semen produced from the ejaculation in the semen collecting device.

An aspect of an embodiment of the present invention provides a method for analyzing the semen collected in the device. The method includes: providing a surface; depositing the semen sample collected in the device on the surface; and analyzing the semen sample deposited on the surface.

These and other objects, along with advantages and features of the invention disclosed herein, will be made more apparent from the description, drawings, and claims that follow.

BRIEF SUMMARY OF THE DRAWINGS

The foregoing and other objects, features and advantages of the present invention, as well as the invention itself, will be more fully understood from the following description of preferred embodiments, when read together with the accompanying drawings in which.

DETAILED DESCRIPTION OF THE INVENTION

Figure 1:
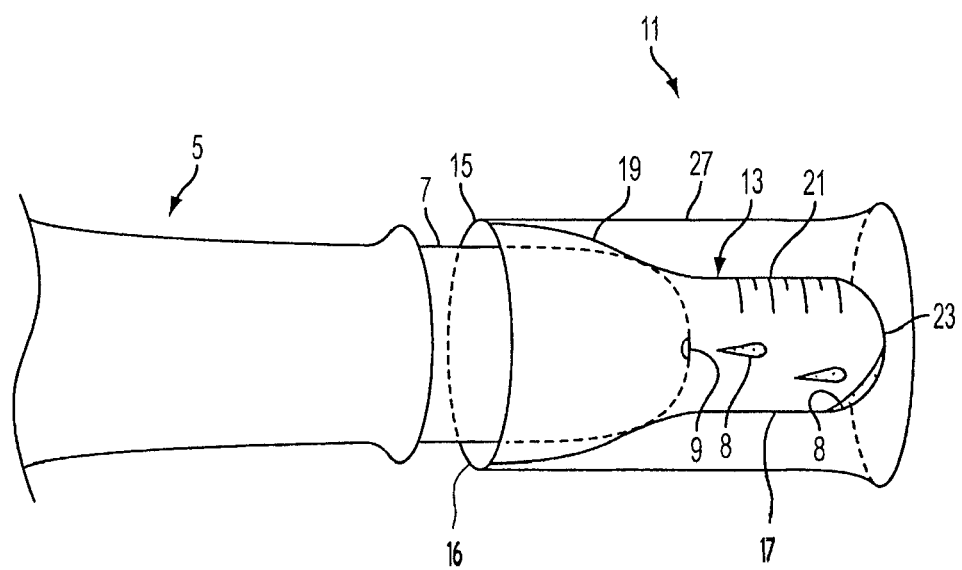
FIG. 1 is a schematic illustration of an embodiment of the collection device in relation to a male glans.

The fertility potential of a human male can be analyzed by examining a semen sample. Semen normally contains sperm from the epididymides as well as seminal plasma contributed by the male accessory sex glands including Cowper's, prostate and seminal vesicle. Semen analyses are essential for evaluation of male infertility, effectiveness of male contraceptives, successful vasectomy or a vas reanastomosis (vas-ovasostomy). Semen samples are also required from donors or the male partner for in vitro fertilization (IVF), intra-cytoplasmic sperm injection (ICSI), intrauterine insemination (IUI), other artificial insemination (AI) procedures or as may be required in forensic case work from suspects or donors. Semen samples are usually obtained by manual masturbation, coitus interruption or by coitus with a condom. However, collecting semen in a condom by coitus may not be an option for certain persons. Furthermore, collection of semen in a condom by coitus or by masturbation results in loss of semen in the condom as well as on the skin of the penis. On the other hand, masturbation into a test tube or in a bottle may also lead to the loss of the sperm concentrated in the initial semen fractions and result in incomplete semen evaluations. Collection of semen samples by condom with transfer to a test tube through a standard funnel also involves multiple transfer related steps and has the likely potential for sample loss and inaccurate semen analysis. Loss of initial fractions may significantly affect semen analysis values, particularly sperm count and motility of a semen sample. Therefore, it is very important to recover the entire ejaculate, specially the sperm rich initial epididymal fluid fractions for sample evaluation despite the manner of collection. Unfortunately, however, no single device is available that prevents loss of semen samples during sample collection and thus optimizes semen collection and subsequent testing.

Some of the embodiments of the present invention provide, among other things, a semen collection device and related method particularly useful for samples collected by masturbation (or other stimulation). The device and method eliminate the loss of semen samples during ejaculation, eliminate loss due to multiple sample transfer steps that follows ejaculation into a condom or into a funnel, allow the sample to liquefy in the storage reservoir without requiring any transfer and also provides a determination of the ejaculate volume directly from the calibrated reservoir.

The various embodiments of the present invention device include a glans penis compatible semen ejaculation cup molded to accommodate the head of the penis (or any other portion of the penis as desired/required) during ejaculation and, optionally, in conjunction with a gripping means, structure or capability for the application of force to oppose the glans penis to the glans accommodating portion of the collection device, to prevent loss of any fractions of semen during ejaculation. For instance, the urethra is optimally aligned with the desired/required location of the glans accommodating portion of the device and/or optimally aligned with the desired/required location of the reservoir of the device. The various attributes are deemed essential because semen comes in split fractions, all of which go directly to the graduated sample reservoir tube. In some embodiments, subsequent collection devices or chambers may be used to collect the ejaculate in split fractions so that, for example, the initial sperm rich fractions of sub-fertile person can be used for fertilization treatment. The entire system of some of the embodiments of the present invention may be a single piece (i.e., integral) molded of soft transparent plastic that may be sterilized. This device may also be utilized as a sterile system that is compatible with the needs of IVF, ICSI and artificial insemination clinics, etc. It should be appreciated that the device can be comprised on any number of individual modules that may be attachable and/or detachable.

Referring to FIG. 1, FIG. 1 is a schematic illustration of an embodiment of the collection device 11 (SPERMCOLLECT collecting device, for example) that provides the capability to collect semen samples by masturbation or coitus interruption (or other stimulation) and to prevent loss of semen during ejaculation. The collection device 11 includes a chamber 13 generally having a proximal end and distal end, thus providing a conduit 17 essentially there between. The proximal end of the chamber 13 having a rim 15 defining an aperture 16, while the distal end of the chamber 13 having a surface 23 that encloses the conduit 17. To use the collection device 11 properly, the glans accommodating portion 19 of the chamber 13 needs to be at least partially placed over the head 7 of the penis 5 (or in contact with the head 7 of the penis 5) following erection or sufficiently prior to ejaculation. This placement causes the orifice 9 of the urethra to be oriented into or along the conduit 17, particularly the glans accommodating portion 19 and/or reservoir section 21, to prevent any backflow of semen during ejaculation. As masturbation (or possibly other stimulation) is continued, the glans accommodating portion 19 is kept over (or in contact with) the glans head 7 until the completion of ejaculation. The ejaculated semen 8 goes directly into a reservoir section 21 of the conduit 17 preventing any backflow. During ejaculation the glans accommodating portion 19 is held over the glans 5 by pressure exerted by the male human individual (or partner) holding the collection device 11 or a partner (or alternatively the device is stabilized or anchored on some surface or interface). The male individual (or partner or anchor) may hold the collection device 11 at any part thereof such as the collar 27 (or adapter section, leg or any protruding member, which is not shown in FIG. 1), glans accommodating portion 19, reservoir 21 or chamber 13. Alternatively, the collection device 11 may be held, stabilized or anchored in place on a surface 31 or any other interface (neither of which is shown) during ejaculation. Moreover, the collection device 11 may be held in place on the glans 5 by a retaining member or apparatus (such as, but not limited thereto, a strap, tape, belt, etc.) for holding the collection device 11 (neither of which is shown).

After ejaculation or a desired duration the collection device 11 can then be placed on a flat surface (or held in desired position) or any interface for spontaneous liquefaction of semen. For instance, but not limited thereto, the spontaneous liquefaction shall be provided to occur at approximately room temperature or in a 37° C. incubator (if available) for about 20 to about 30 minutes. It should be appreciated that any type of commercially available incubator (or apparatus for desired process) may be utilized as well. Moreover, the liquefaction period may be any desirable or required duration. Additionally, the temperature of any of the related processes may be adjusted as necessary or desired.

The collection device 11 may also be used in conjunction with condom based collection by masturbation, stimulation or intercourse. Following ejaculation in a condom, it can be at least partially placed in the glans accommodating portion 19 (and/or reservoir 21) of the collection device 11 after cutting or puncturing the tip or other part of the condom with a scissor or the like. This allows the semen to be recovered in the reservoir section 21 of the conduit 17 following liquefaction. However, it should be appreciated that attempting to squeeze the unliquefied semen from the condom to the collection device 11 may result in greater loss of semen (unliquefied part contains entrapped sperm) in the condom in addition to the loss of semen on the penile skin. Following liquefaction of the semen in the reservoir section 21, the sample may be (including any of the embodiments discussed throughout) thoroughly mixed by a dropper, a pipette, a vortex mixer, or other available tools/instruments prior to semen evaluation for sperm count, motility, viability and relative secretions from the accessory sex glands. Alternatively, any available process may be applied to the sample while in the conduit 17 or after it has been removed.

Some of the advantages of some of the embodiments of the present invention semen collection and storage device, and related method of use are multifold. For example, but not limited thereto, freshly ejaculated human semen is a heterogeneous mixture of fluid and gel phases that entrap spermatozoa in a relatively immotile state before liquefaction. During ejaculation, human semen is produced in split fractions which follow a specific sequence of emission with the orgasmic contractions. The initial fractions are contributed by the Cowper's secretion followed by highly sperm rich epididymal secretions and some prostate secretion, followed by fractions containing mixture of prostatic and seminal vesicular secretions and finally the ejaculate culminates with soft gel-like coagulum primarily contributed by seminal vesicular secretion. The various embodiments of the collection device eliminate the unesthetical condom use during masturbation, prevents loss of sperm rich initial fractions during conventional collection into a test tube or into a bottle and also avoids multiple transfer related sample loss following ejaculation into a condom.

Some of the embodiments of the present invention collection device are made of a soft, flexible and transparent polyethylene or similar material to monitor complete sample recovery following ejaculation. It should be appreciated that the device may be hard, rigid and opaque material as well. Moreover, it should be appreciated that the collection of device or parts thereof may be comprised of any variety of commercially available materials and have a structure(s) with a wide range of rigidity that which is necessary to accomplish its operation.

The glans compatible portion 19 provides the capability, among other things, to prevent any potential loss of sperm rich initial fractions. The conduit 17 includes a graduated semen reservoir 21 tube that is suitable for holding and measuring any seminal volume. For instance, in an embodiment the seminal volume may range from ≦1.0 ml to about 10.0 ml or ranging from 0.5 ml to about 15 ml. It should be appreciated that any desired/required volume may be utilized. Following sample collection, the unit can be kept on a flat surface 31 (or any accommodating surface) for spontaneous semen liquefaction to occur before analysis/examination of the sample. In some embodiments the collection device 11 may be one integral unit (i.e., single unit) that helps eliminate the extra manufacturing and assembly steps associated with multiple collection components such as those contained in the available semen collection systems. Similarly, in some embodiments two or more of any components discussed throughout this document regarding the embodiments of the present invention may be integrally formed (i.e. single unit).

It should be appreciated that variations within reasonable ranges may be practiced so long as the broader aspects of the present invention are accommodated, particularly where such variations are desired or necessary to accommodate differing physical or subjective requirements of respective users.

Another advantage associated with at least some of the embodiments of the present invention is that it can be readily sterilized because of its size, material, shape, and/or integration. Due to, among other things, the readiness of the collection device 11 to be sterilized, the collection device 11 is also compatible with desired collection requirement for in vitro fertilization, intra cytoplasmic sperm injection and artificial insemination procedures, as well as any other applicable procedures. The collection device 11 is more user friendly than condom mediated collection. This collection device 11 may cover only the head part of the penis during masturbation unlike the condom which covers the entire length and therefore interferes minimally with the natural sensation during masturbation. The device is very easy to put on and take off at any time during use and semen collection steps. Alternatively, as well be discussed later with regards to FIG. 10, for example, an augmentation/adapter section may be added to the collection device 11.

In assisted reproduction (like, in vitro fertilization (IVF), intra-cytoplasmic sperm injection (ICSI), artificial insemination (AI)), male partners with low sperm count are often required to ejaculate in split fractions so that the initial fractions, which are rich in sperm count, may be collected and isolated. Because of its unique design and the ease with which it may be removed from the penis, the present invention collection device 11 would also be very appropriate for the collection of initial fractions required for assisted reproduction in cases where a split ejaculate is needed.

Following ejaculation, the collection device 11 allows spontaneous (or subsequent) liquefaction and complete recovery of ejaculated material, provides the measurement of the ejaculated volume, provides for the mixing of sperm and liquefied seminal plasma components for subsequent semen analysis and cryo-preservation of the sample. This collection device 11 is suitable for use in, but not limited thereto, hospitals, clinics, semen analysis laboratories, fertility and infertility diagnostic laboratories, IVF, ICSI and AI clinics, vasectomy clinics, basic research laboratories, forensic (crime) research labs, prisons and also by home test users.

Figure 2A:
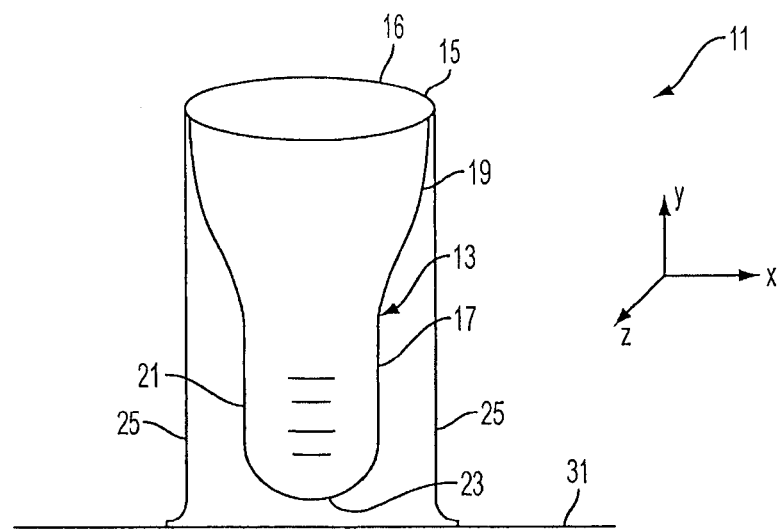
FIGS. 2(A)-(B) are schematic illustrations of embodiments of the collection device having at least one protruding member, wherein the protruding member is at least one leg-like structure or collar-like structure, respectively.
Figure 2B:
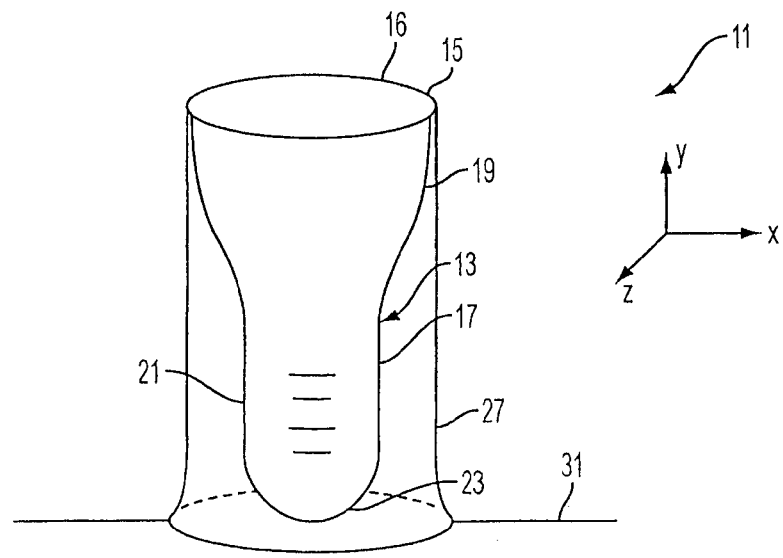

Turning to FIGS. 2(A)-(B), FIGS. 2(A)-(B) are schematic illustrations of embodiments of the collection device 11. The collecting device 11 for collecting semen received from a glans penis of a male human individual having a chamber 13 generally having a proximal end and distal end, with a conduit 17 essentially there between. The proximal end of the chamber 13 having a rim 15 defining an aperture 16, while the distal end of the chamber 13 having a surface 23 that encloses the conduit 13. At least a portion of the conduit 17 proximal to the proximal end having a tapered shape radially inward defining a tapered section (or may be a flared section, for example) that forms a glans accommodating portion 19. At least a portion of the conduit 17 proximal to the distal end is adapted for receiving the semen ejaculated from the glans penis that forms a reservoir section 21 for the semen to accumulate. After or during the semen is collected into the collection device 11, the collection can stand upward on suitable protrusion members such as at least one leg 25 as schematically represented in FIG. 2(A) or at least one collar 27 as schematically represented in FIG. 2(B). It should be appreciated that various types of leg-like members or collar-like members may be suitable for standing the collection device upward. The bottom of the collar 27 of FIG. 2(B) may be open or closed or a combination thereof.

The glans accommodating portion 19 may be a variety of shapes and sizes to accommodate the head of the glans penis (not shown) so that an effective tight fit can be achieved with the head of the glans penis. For example, the shape may be bell-shaped, olive shaped, hemispherical shaped, ellipsoid shaped or multifaceted shaped, cone shaped, etc. The sides or walls of the glans accommodating portion 19 may be curved, multicurved, sloped, multifaceted, beveled, sloped, chamfered, flared or the like. For instance, the sides or walls of the glans accommodating portion 19 may be shaped along the entire geometric spectrum of potential shapes x, y and z planes.

Figure 3A:
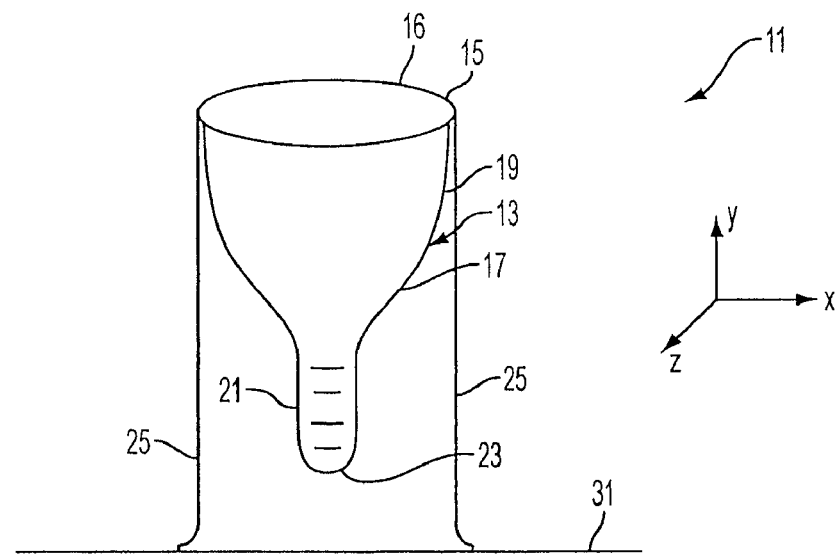
FIGS. 3(A)-(B) are schematic illustrations of embodiments of the collection device having at least one protruding member, wherein the protruding member is at least one leg-like structure or collar-like structure, respectively.
Figure 3B:
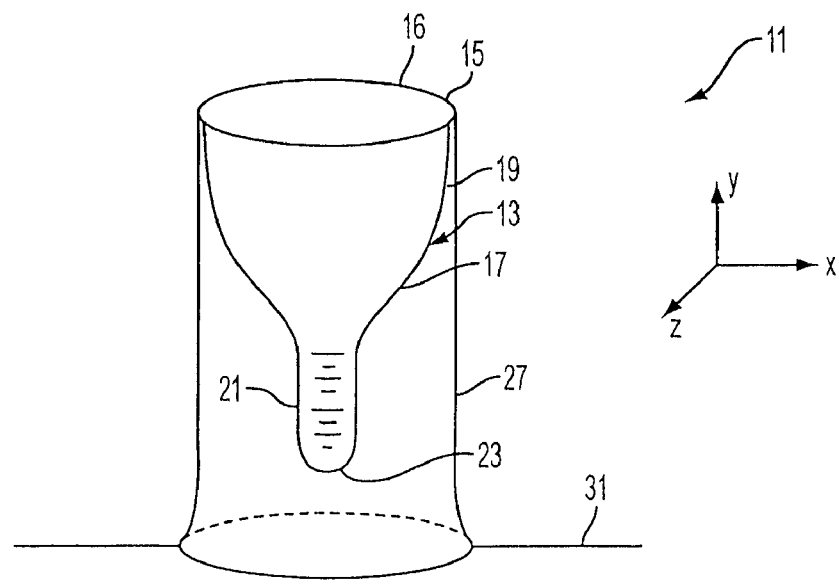

Turning to FIGS. 3(A)-(B), FIGS. 3(A)-(B) are schematic illustrations of embodiments of the collection device 11 similar to the device shown in FIG. 2 with the exception, for example, that reservoir section 21 has a maximum cross-section smaller than the shortest cross-section of the glans accommodating portion 19.

Figure 4A:
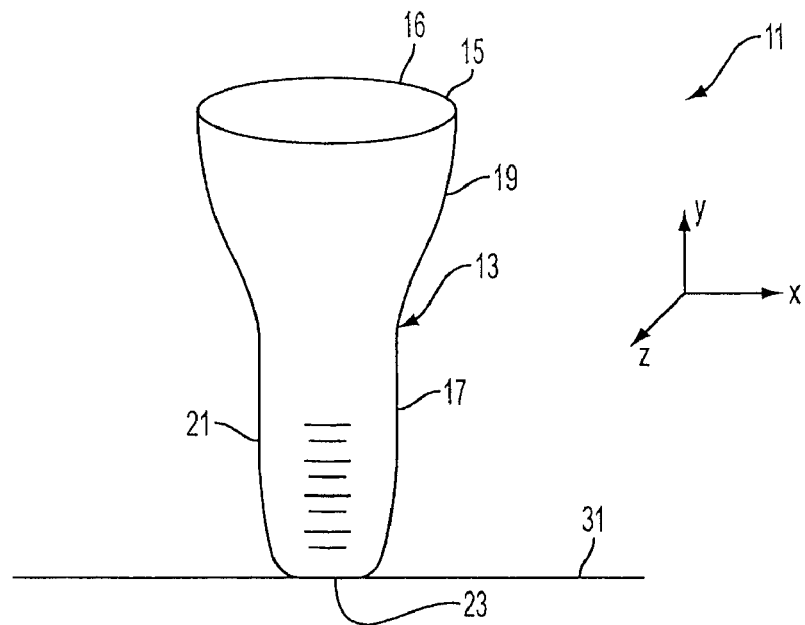
FIGS. 4(A)-(B), are schematic illustrations of embodiments of the collection device 11 wherein the bottom of the chamber is at least substantially flat.
Figure 4B:
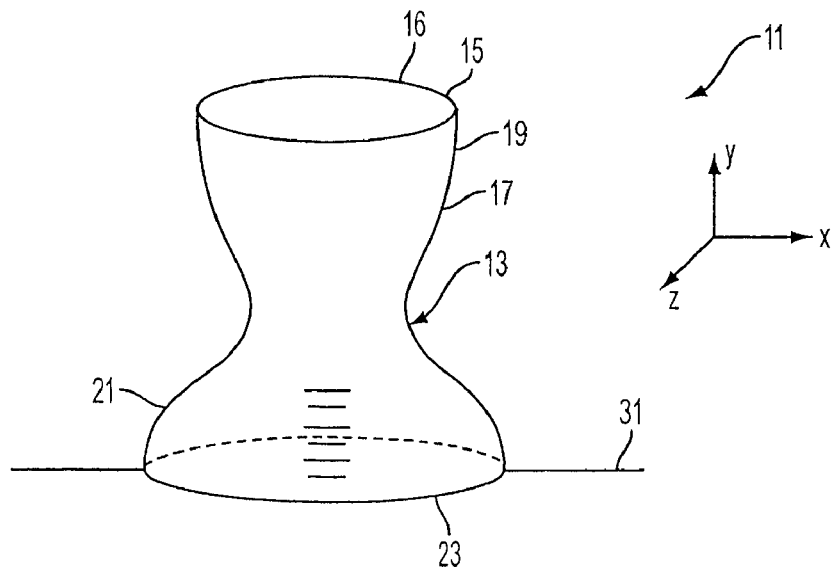
Figure 13A:
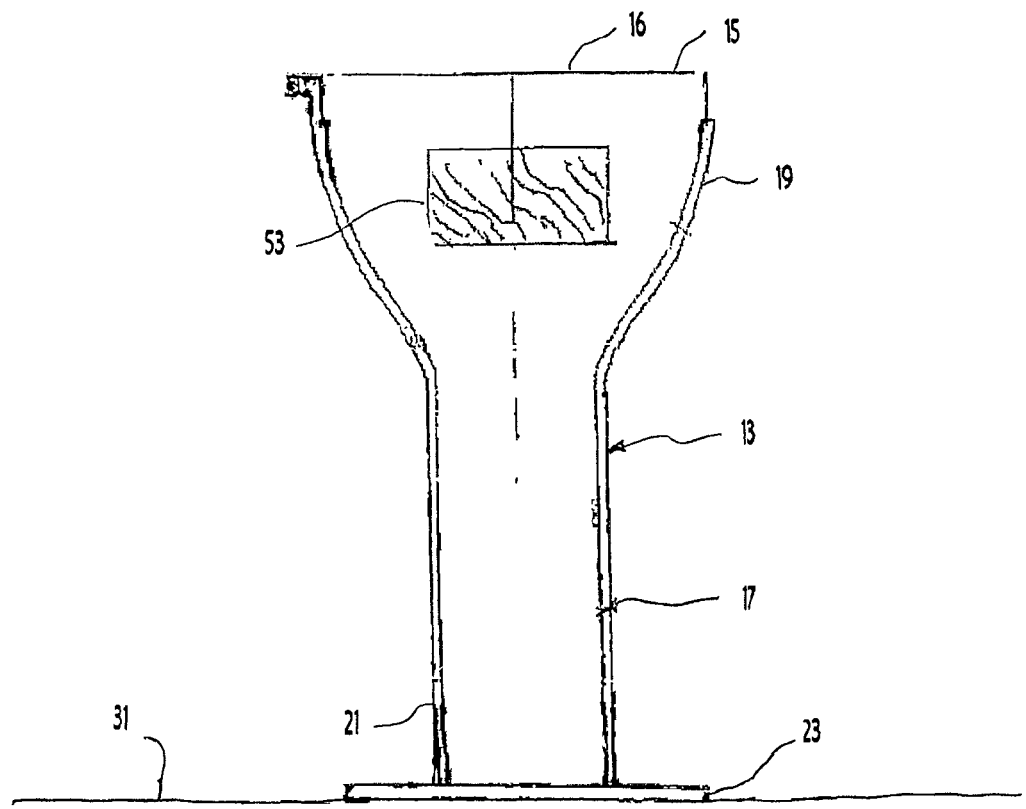
FIG. 13(A) is a schematic illustration of an embodiment of the collection device wherein the bottom of the chamber is at least substantially flat.
Figure 13B:
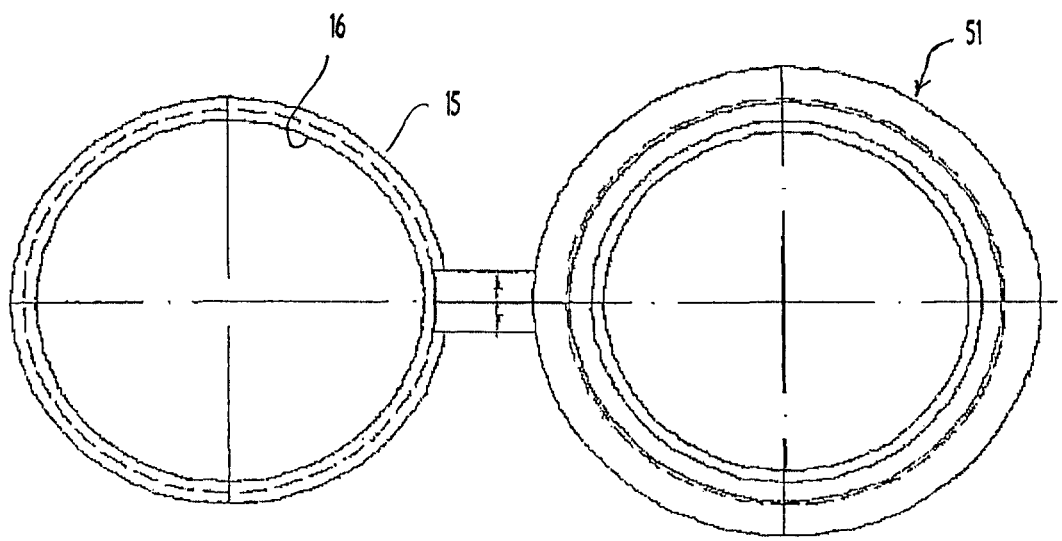
FIG. 13(B) is a plan view of the embodiment of FIG. 13(A).

Turning to FIGS. 4(A)-(B) and FIG. 13(A), FIGS. 4(A)-(B) and FIG. 13(A) are schematic illustrations of embodiments of the collection device 11 wherein the bottom 23 of the chamber 13 is at least substantially flat as shown, for example, so as to be able to stand upward on a surface 31 (for example as a flat surface, such as a desk, counter, table, bed, or any desired surface). Similarly, the bottom 23 of the chamber 13 (or any part of the chamber) may be contoured (not shown) so that it may stand upward on various shaped interfaces or surfaces as required. Moreover, although not shown, there maybe a peg or any attachment device means provided for securing or anchoring the collection device 11 to an interface. Alternatively, the entire collection device or chamber is anchored or secured in a recess of an interface surface (or to an interface surface). FIG. 13(A) is a schematic illustration of an embodiment of the collection device 11 with the addition of a lid or cap 51. FIG. 13(B) is a corresponding plan view of FIG. 13(A) of the collection device 11 and lid or cap 51, or the like.

Figure 6:
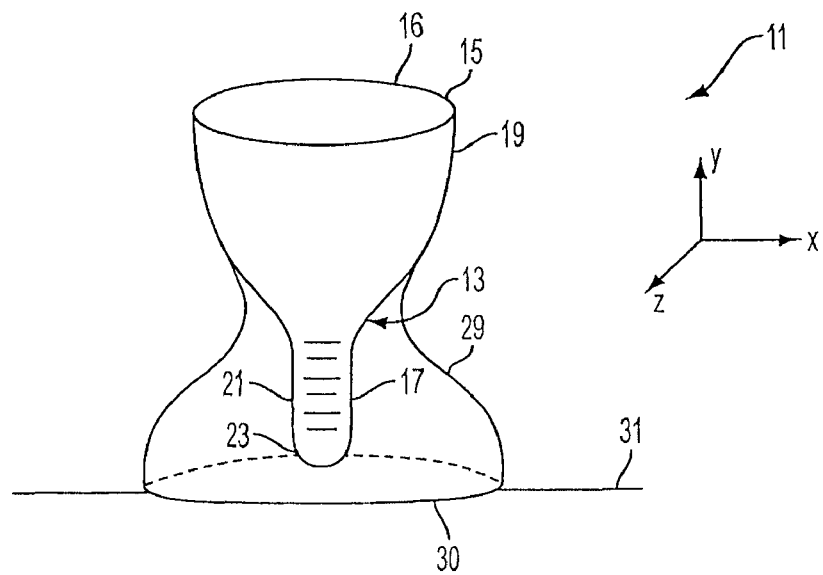
FIG. 6 is a schematic illustration of an embodiment of the collection device 11 including a reservoir having a bottom that is a distinct from the base of the overall collection device.

Turning to FIG. 6, FIG. 6 is a schematic illustration of an embodiment of the collection device 11 similar to the device shown in FIG. 4(B) with the exception, for example, the reservoir 21 is a distinct compartment from the base 30 of the collection device 11.

Figure 14A:
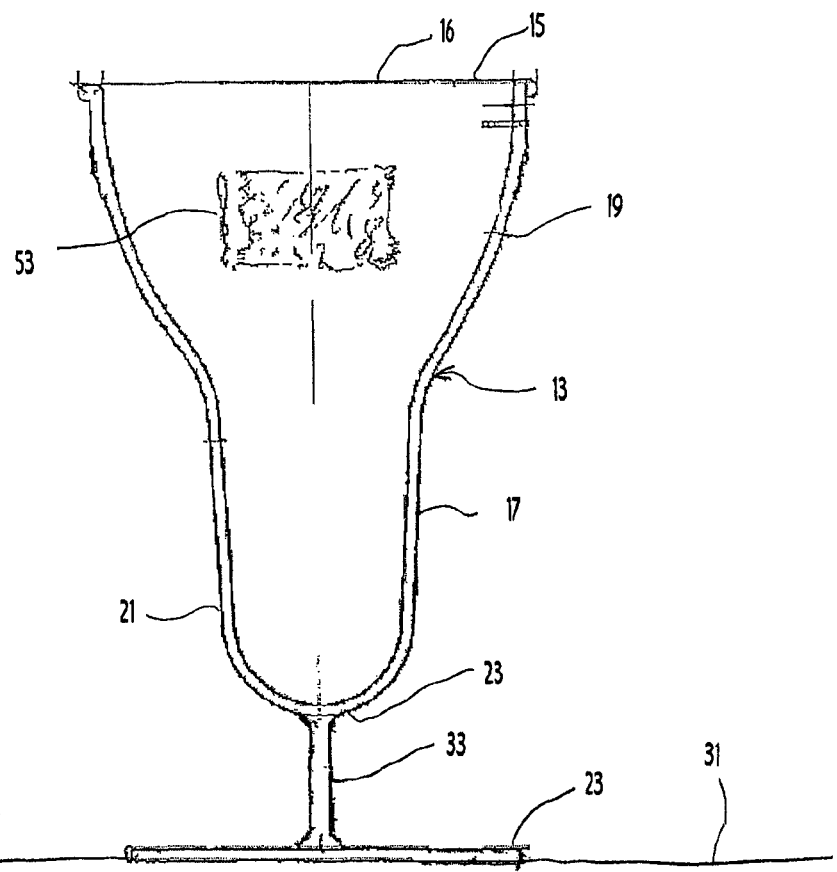
FIGS. 14(A) and 15(A) are schematic illustrations of various embodiments providing an exemplary approach for stabilizing the collection device.
Figure 14B:
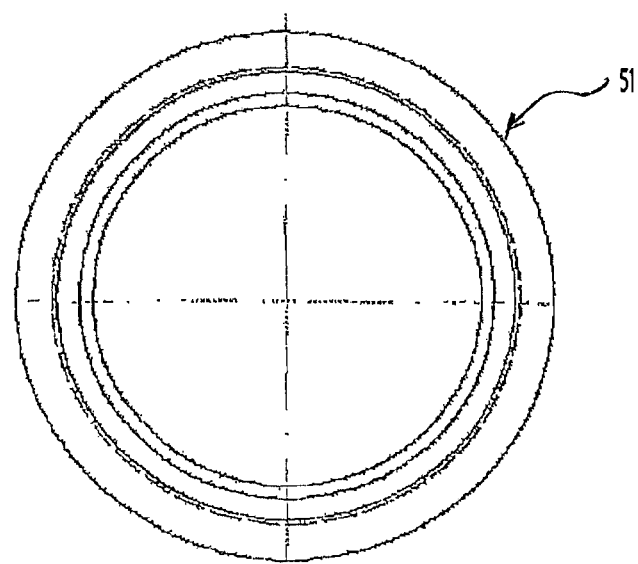
FIGS. 14(B) and 15(B) are plan views of the embodiments of FIGS. 14(A) and 15(A), respectively.
Figure 15A:
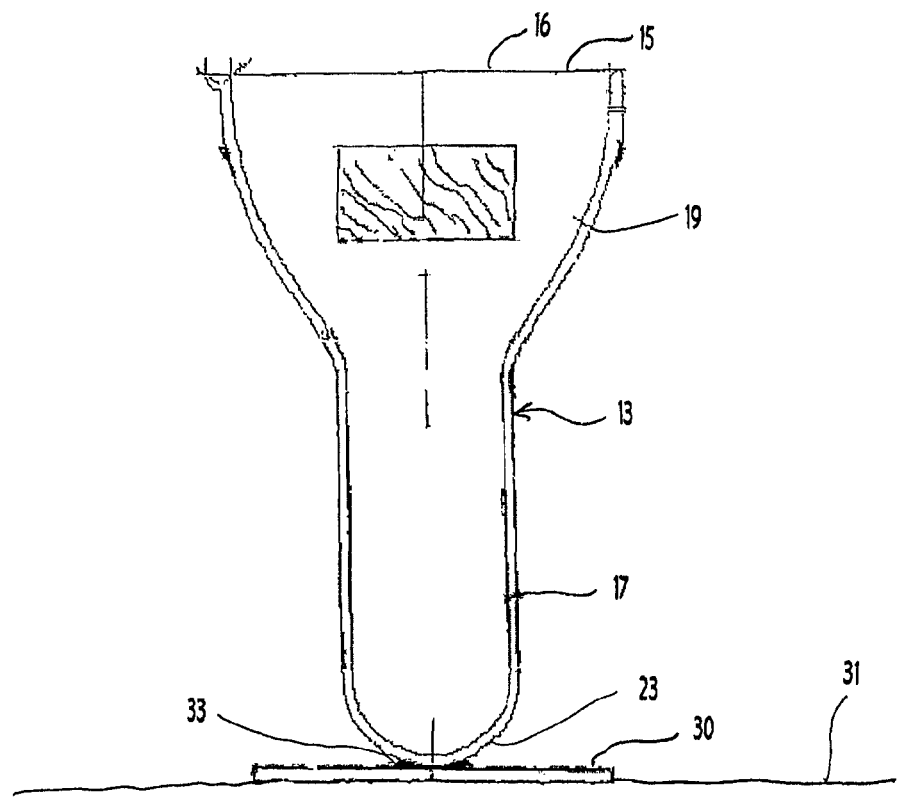
Figure 15B:
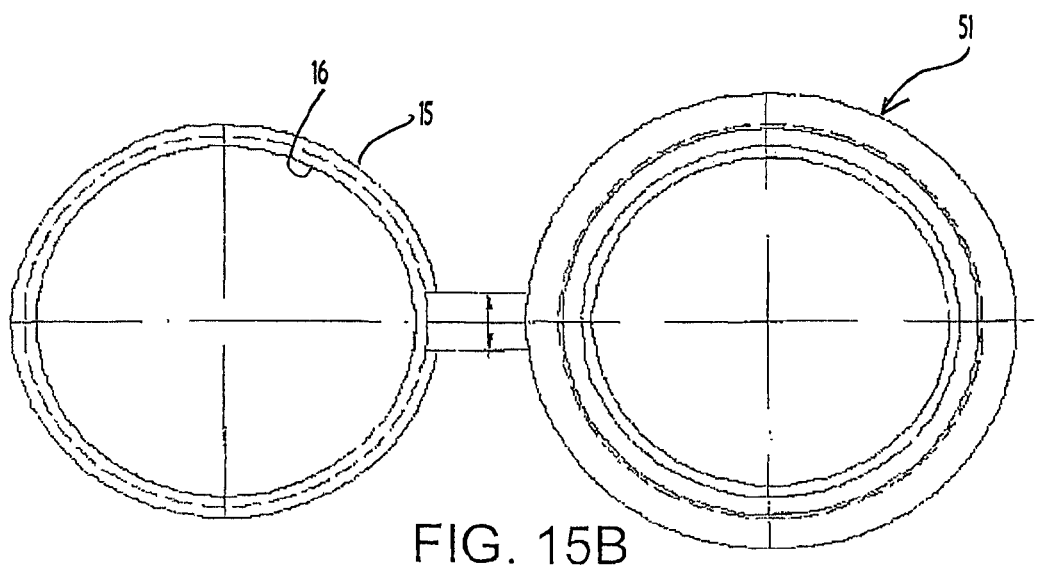

Similarly, FIGS. 14(A) and 15(B) are schematic illustrations of embodiments of the collection device 11 wherein the base 30 is connected to the reservoir 21 using other exemplary manners. For instance, FIG. 14 reveals a connector 33 utilizing a leg, stem or the like. Whereas, FIG. 15 reveals a connector 33 utilizing adhesion, brazing, soldering, welding, plastic forming, or any joining technique, material or structure. FIGS. 14(B) and 15(B) are corresponding plan views of the collection device of FIGS. 14(A) and 15(A), respectively, wherein the collection device 11 includes a lid or cap 51, or the like.

Figure 5:
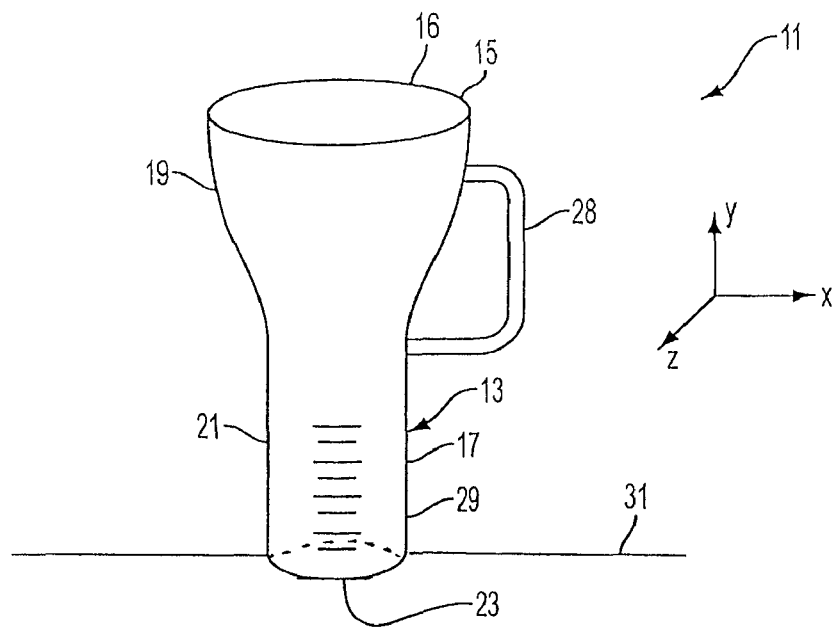
FIG. 5 is a schematic illustration of an embodiment of the collection device including a handle or the like disposed thereon.

Turning to FIG. 5, FIG. 5 is a schematic illustration of an embodiment of the collection device 11 having a handle 28 for the male individual and/or partner to hold before, during or after ejaculation for example. The handle 28 may be disposed anywhere on the collection device 11. It should be appreciated that the handle may be a variety of shapes including grips, tabs, grip ridges, straps, knobs, or the like and made of variety of commercially available materials having suitable properties for strength and/or grip/adhesion. It should be appreciated that the handle 28 may be a variety of shapes to accommodate the grasp of a person or mechanical device. Moreover, it should be appreciated that, although not shown, the entire collection device or substantial part there of may have the outside surface contoured for easy grasp or anchoring.

Figure 7:
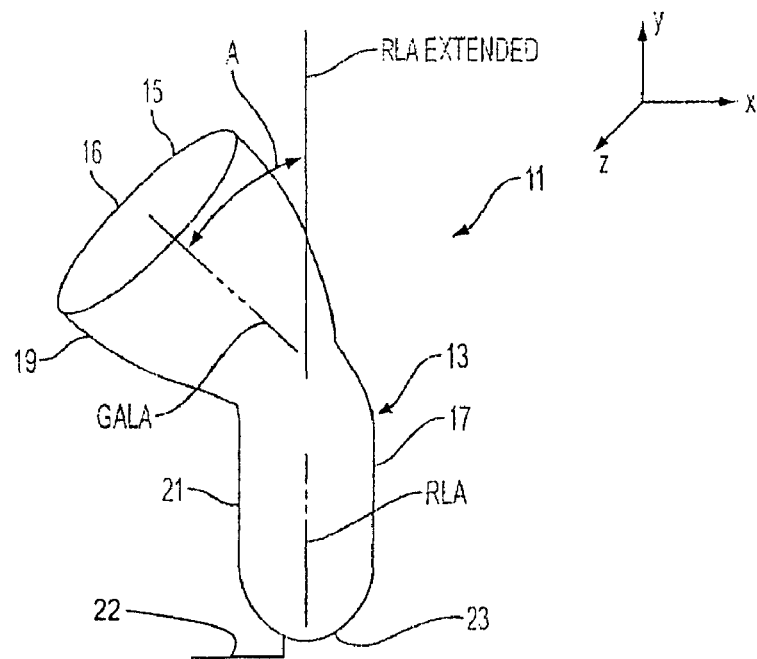
FIG. 7, is a schematic illustration of an embodiment of the collection device having glans accommodating portion tilted relative to the reservoir.

Turning to FIG. 7, FIG. 7, is a schematic illustration of an embodiment of the collection device 11 having glans accommodating portion 19 tilted relative to the reservoir 21. It should be appreciated that the glans accommodating portion 19 may be adapted so as to be generally parallel with the reservoir (as shown in the previous figures) or may be oriented to form an elbow relative to the reservoir 21 having a bend at the necessary or required angle. For illustration purposes only, a reservoir longitudinal axis (RLA) is depicted and a glans accommodating longitudinal axis (GALA) is depicted. The elbow formed is represented by the angle referenced as A, i.e., the angle formed between the RLA extended and the GALA.

Figure 8:
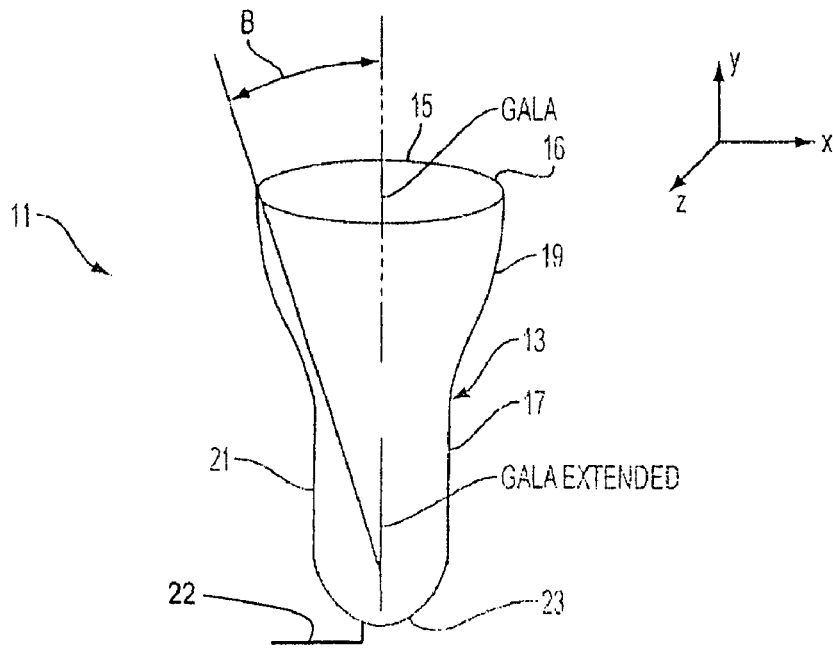
FIG. 8, is a schematic illustration of an embodiment of the collection device having glans accommodating portion wherein a geometric spectrum of potential shapes x, y and z planes is schematically illustrated.

Turning to FIG. 8, FIG. 8, is a schematic illustration of an embodiment of the collection device 11 having glans accommodating portion 19. For illustration purposes the GALA and the GALA extended is depicted. As mentioned previously, the glans accommodating portion 19 may be a variety of shapes and sizes to accommodate the head of the glans penis (not shown) so that an effective tight or desired/required fit can be achieved with the head of the glans penis. For example the shape may be bell-shaped, olive shaped, hemispherical shaped, ellipsoid shaped or multifaceted shaped, cone shaped, etc. The angle formed between the GALA extended and general slope of the sides of the glans accommodating portion 19 is represented by the angle referenced as B. Angel B may range, for example, between 0 degrees and about 75 degrees, or any desired or required limit. The sides or walls of the glans accommodating portion 19 may be shaped along the entire geometric spectrum of potential shapes in the x, y and z planes.

Figure 10:
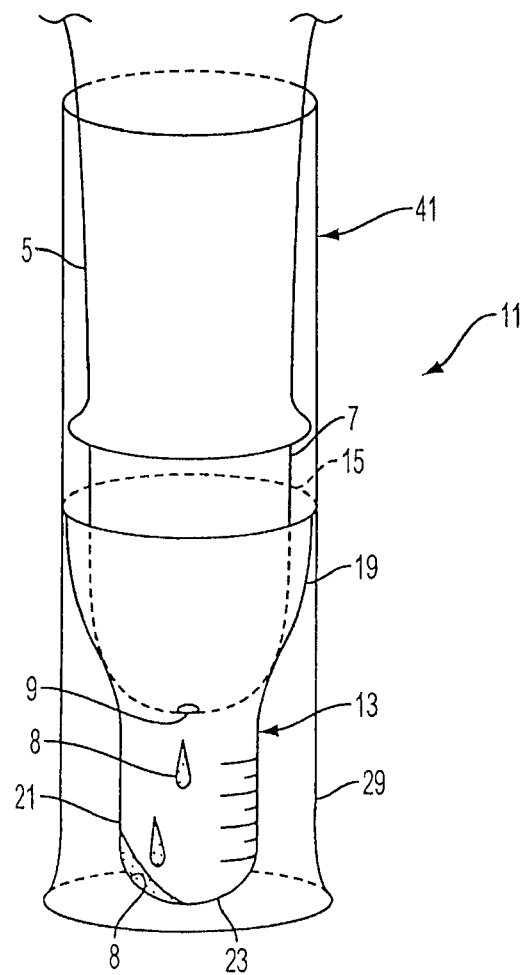
FIG. 10 is a schematic illustration of an embodiment of the collection device with the addition of an adapter section.

Turning to FIG. 10, FIG. 10 is a schematic illustration of an embodiment of the collection device 11 similar to the device shown in FIG. 1 with the addition of an adapter section 41. The adapter section 41 may be, for example, an addition to the glans accommodating portion 19 such as for added grip, comfort, stimulation, coverage, etc., or any desired or required purpose. For instance the adapter section 41 may be provided with a lining, fluid, lubricant, jacket, inflatable jacket, inflatable lining. Moreover, the adapter section 41 may be, for example, the stimulation devices shown in the following U.S. patents of which are hereby incorporated by reference herein in their entirety: U.S. Pat. No. 6,149,580 to Dabney, entitled "Medical Device to Aid in Ejaculation;" U.S. Pat. No. 6,113,532 to Yap, entitled "Ejaculation Aid and Sperm Collection Device;" U.S. Pat. No. 5,501,650 to Gellert, entitled "Automated Masturbatory Device;" For example, the adapter section 41 may be at least partially the core member and surrounding member of the medical device to aid in ejaculation similar to U.S. Pat. No. 6,149,580 to Dabney. For example, the adapter section 41 may be at least partially panels of the ejaculation aid and sperm collection device similar to U.S. Pat. No. 6,113,532 to Yap, with the exception that an aperture is provided in communication with the chamber 13. For example, the adapter section 41 may be at least partially the receiver with a tube for an automated masturbating device similar to U.S. Pat. No. 5,501,650 to Gellert.

Figure 9:
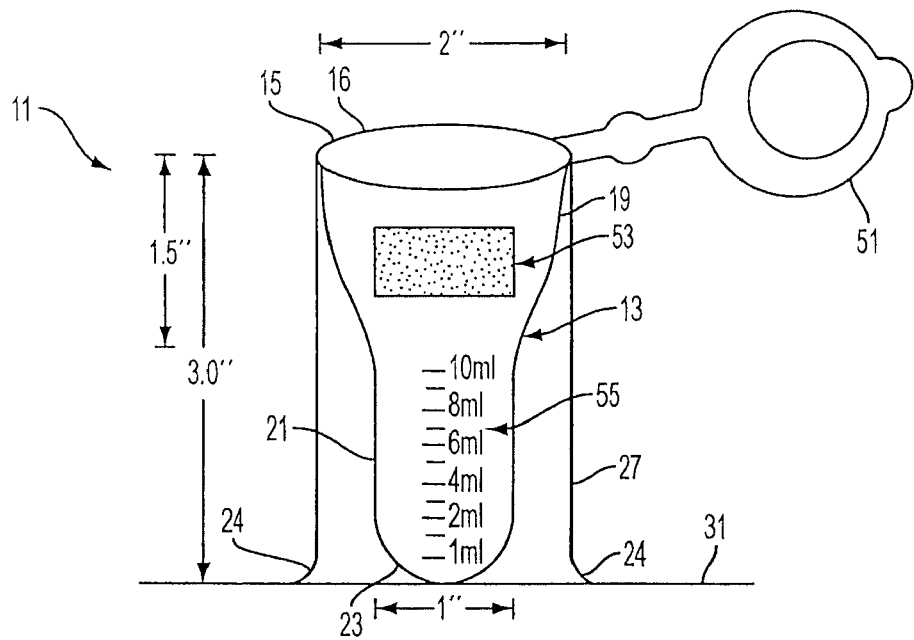
FIG. 9 is a schematic illustration of an embodiment of the collection device 11 with the addition of a lid or cap, along with non-limiting dimensions that are intended to be illustrative only.

FIG. 9 is a schematic illustration of an embodiment of the collection device 11 with the addition of a lid or cap 51. The lid, cover or cap 51 may be utilized for containing the semen sample in the chamber 13 during transportation and/or storage. Moreover, the lid, cover or cap 51 may be utilized for keeping the interior of chamber 13 sterile. Although not shown, it should be appreciated that in some embodiments, the glans accommodating portion and the reservoir section may be detachable and/or attachable. Further a cap, lid or cover may also be provided to be placed on the reservoir section rather than or in addition to the glans accommodating portion cover. Moreover, in some embodiments some if not all of the components of the collecting device may be attachable/detachable. In some embodiments the cap or cover may be placed on the glans accommodating portion or the reservoir section. In at least an embodiment, a frosted surface 53 or bar code system or any tracking means may be provided on the chamber 13 that permits labeling or tracking the semen collector's name, time of collection, the period of abstinence, semen volume, other information or parameters, etc. In at least an embodiment, at least a portion of the chamber 13 has a volume measure/indicator means 55 (calibrated reservoir), such as graduated in milliliters or ounces (or any means for measuring semen volume) to determine sample volumes.

Figure 11A:
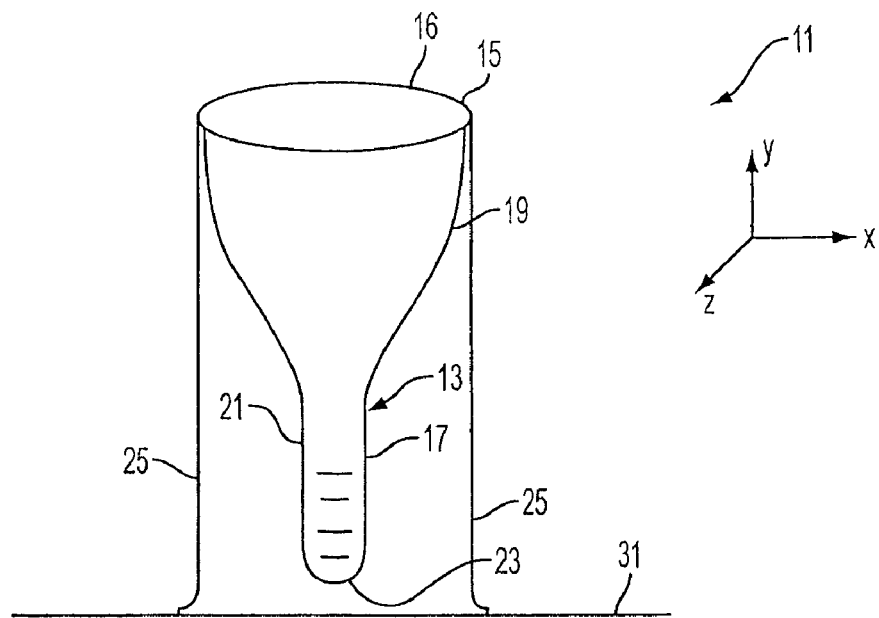
FIGS. 11(A)-(B) are schematic illustrations of embodiments of the collection device having at least one protruding member, wherein the protruding member is at least one leg-like structure or collar-like structure, respectively.
Figure 11B:
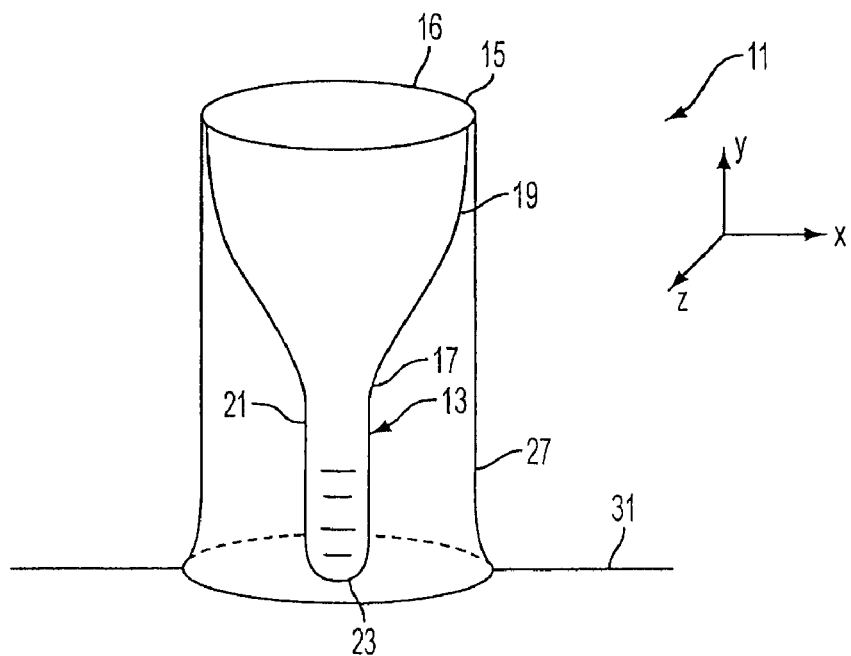

Turning to FIGS. 11(A)-(B), FIGS. 11(A)-(B) are schematic illustrations of embodiments of the collection device 11 similar to the device shown in FIG. 2 with the exception, for example, the reservoir section 21 has a cross-section that generally tapers from a larger cross-section to a shorter cross-section traveling in a direction away from the glans accommodating portion 19.

Figure 12A:
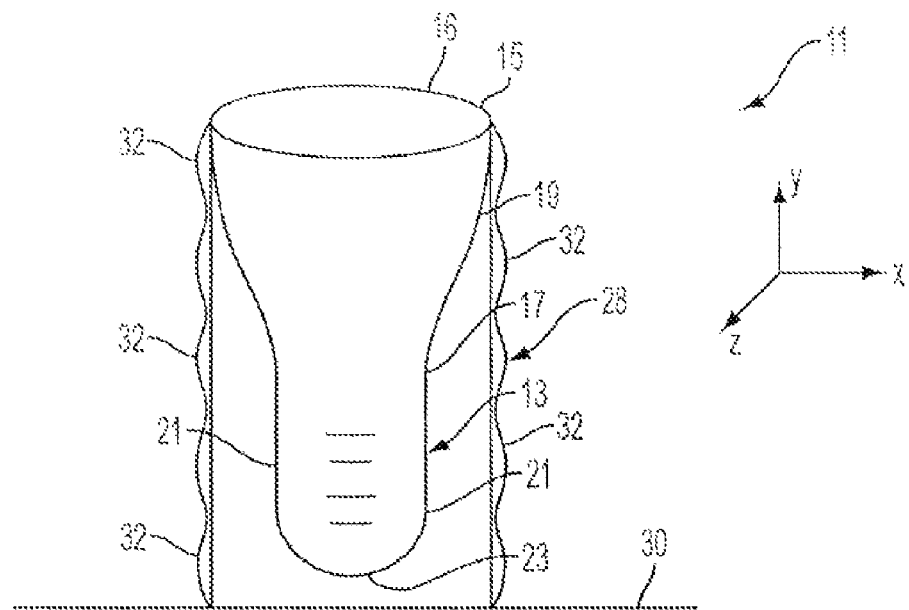
FIGS. 12(A)-(B) are schematic illustrations of embodiments of the collection device having grip ridges.
Figure 12B:
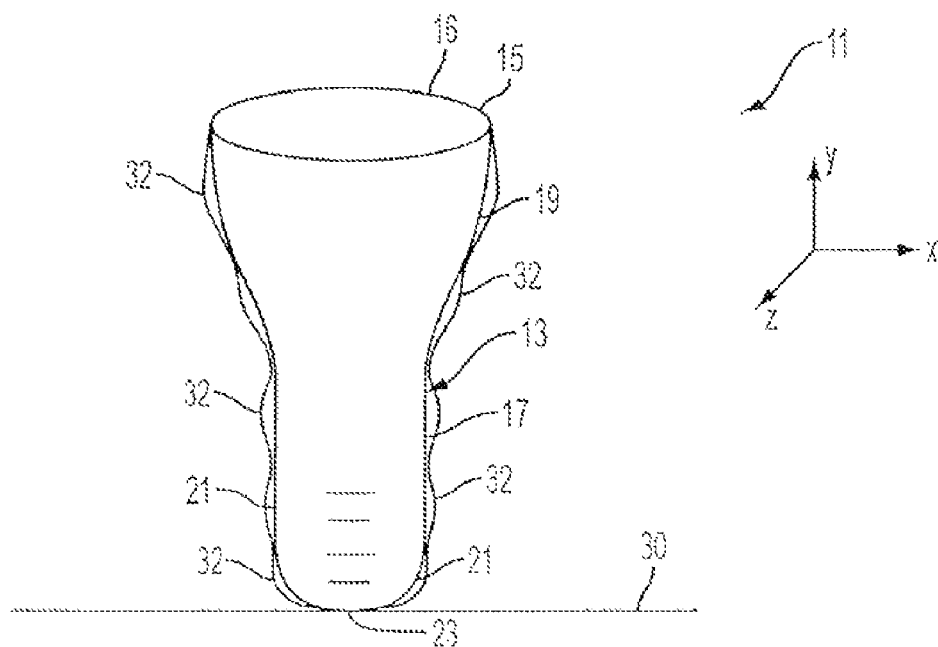

Turning to FIGS. 12(A)-(B), FIGS. 12(A)-(B) are schematic illustrations of embodiments of the collection device 11 having at least one grip ridge 32 for the male individual and/or partner to hold before, during or after ejaculation for example. The grip ridges 32 may be disposed anywhere on the collection device 11, such as the glans accommodation portion 19, adapter section 41 (not shown in present figures), reservoir 21, and/or protruding member 29 (e.g., legs, collar, or the like). It should be appreciated that the grip ridges 32 may be a variety of shapes to accommodate the grasp of a person or mechanical device, and made of variety of commercially available materials having suitable properties for strength and/or grip/adhesion/stabilization.

Alternatively, with regards to any of the embodiments discussed throughout, it is feasible that a port is provided on the reservoir to allow for drainage or other access or communication to the collected sample. The port may be in communication with various communication channels (or channel) to allow at least partial collected sample to travel through. For example, the communication channel(s) may include any one of the following: a channel(s), microchannel(s), capillary tube(s), microtubing(s), tubing(s), pipette(s), micropipette(s), or column(s), or the like as well as any other systems/devices. For example, but not limited thereto, a communication channel 22 is disclosed in FIGS. 7-8, but it should be appreciated that it may be implemented with any of the embodiments disclosed herein.

Alternatively, with regards to any of the embodiments discussed throughout, it is feasible that part of the reservoir or entire reservoir is a communication channel(s) that may allow at least partial collected sample to travel through. For example, the communication channel may include anyone of the following: channel(s), microchannel(s), capillary tube(s), microtubing(s), tubing(s), pipette(s), micropipette(s) or column(s), or the like as well as any other systems/devices.

Test Kit

Referring to the commonly assigned U.S. Pat. No. 5,605,803 to Herr et al. (herein after "Herr '803"), entitled "Human Sperm Diagnostic," of which is hereby incorporated by reference herein in its entirety, there are a variety of situations in which a test that could be done at home, or in privacy, without the intervention of a medical or scientific practitioner, would be desirable. That in fact such applications are particularly desirable can be confirmed by reference to the enormous success of the home colorimetric urine test for pregnancy, in which the presence or absence of HCG is indicated through a colorimetric test that is quickly and conveniently done by the female wishing to determine whether she is pregnant or not. Similarly, as discussed in detail Herr '803, there are a variety of situations where it would be desirable to be able to determine whether an individual's ejaculate in fact contains sperm, and if so, whether the sperm approaches a threshold value necessary for practical fertility. In these assays, as with the assays discussed in '803 Herr, the presence or absence of sperm can be determined by using one or more monoclonal antibodies specific for a sperm tissue-specific antigen or protein, such as SP-10. Where it is necessary to evaluate whether or not sperm are present in a particular concentration or level, it is fairly easy to calibrate such a test to a standard, below which the reaction is not clearly detectable or visible. In the alternative, where the threshold value is positive, the signal can be reinforced or caused again to change color. The essence of this testing is again the contacting of a sample suspected of containing human sperm with a monoclonal antibody specific for a sperm-specific protein.

Accordingly, the present invention may be utilized as a kit for detecting the presence of sperm in a biological sample, comprising: (1) a surface on which said sample may be deposited, (2) an antibody specific for a testes and sperm tissue-specific protein antigen present throughout spermiogenesis, and (3) a means for indicating binding of said monoclonal antibody to antigen present in said sample. The surface on which said sample may be deposited may be a separate distinct surface (or surfaces). For instance, various embodiments of the present invention may be included as part of, for example, a SPERM CHECK KIT produced by ContraVac Incorporated. Moreover, in some embodiments the present invention collection device may be used with sperm testing kits or any available sperm examination/analyses procedures, systems, or devices for examination/analysis of sperm count, morphology, motility, viability and markers of accessory sex gland secretion. For example, the collection device may be utilized with the kits discussed in U.S. Pat. No. 5,055,411 to Ericsson et al. entitled "Method Used in Testing Human Males for Fertility" and U.S. Pat. No. 5,068,089 to Ericsson et al. entitled "Method Used in Testing Human Males for Fertility," of which are hereby incorporated by reference herein in their entirety.

In summary, the various embodiments of the present invention may be implemented for, but not limited thereto, the following: hospitals, clinics, semen analysis laboratories, fertility and infertility diagnostic laboratories, IVF clinics, ICSI clinics, artificial insemination clinics, vasectomy clinics, anthology research laboratories, basic research laboratories, forensic (crime) laboratories and law enforcement agencies, prisons, home sperm test users, and environmental monitoring for effect of toxins on spermatogenesis in occupations such as mining, agriculture, radiation exposure, industries, etc.

EXAMPLES

The following examples are intended for illustrative purposes and are not intended to be limiting in any manner.

Example No. 1

In at least one exemplary embodiment, the collection device is a free standing sterilizable semen ejaculation device that prevents semen loss during ejaculation and avoids multistep transfers related to sample loss after ejaculation. Still referring to the at least one embodiment, the device is made from soft transparent polyethylene or similar material to reduce cost. The device contains a collecting chamber that accommodates up to a two inch diameter glans penis. This chamber is applied to the glans penis to prevent sample loss during ejaculation. A portion(s) of this chamber is sculptured or configured to accept the contour of the glans penis (heads of the glans penis or other parts of the glans penis). The collecting chamber is fused with a 1 inch diameter (or other dimensions as required) semen storage and volume measuring unit that allows semen liquefaction at room temperature and subsequent sampling for semen analyses. An integral skirt provides support for this semen collection device enabling it to stand alone on any flat surface for subsequent sampling. A projecting rim (e.g., 3/16 inch or other dimensions as required) at the bottom of the skirt provides extra support to the unit for self standing in order to reduce accidental sample spillage. Alternatively, if the device does not have a skirt/collar, the enclosure surface/bottom of the chamber may be contoured with a variety of shapes (as discussed throughout), such as a rim or stand or the like for self-standing or anchoring. The frosted surface on the collecting chamber permits labeling the semen collector's name, time of collection, the period of abstinence, semen volume, etc. The device provides a more user-friendly semen collection system than previous condom based collection by masturbation. The device prevents loss of semen samples associated with collection by masturbation, particularly initial sperm rich fractions and also minimizes transfer related sample loss following collection in a condom. The device may be a single unit device suitable for ejaculation (without condom), semen collection and semen liquefaction all within a single self standing unit. The collecting chamber may be molded to fit the anatomy of the glans penis to accommodate a range of anatomical variants. The device locks onto the glans penis with gentle pressure preventing semen loss. When applied according to instructions, the device prevents any backflow of semen during and following ejaculation. The device eliminates or virtually eliminates the loss of semen samples during collection when used according to directions. The device is ideal for collecting initial fractions rich in concentrated sperm. The device provides for the recovery of up to 100 percent of the semen sample if used according to directions. Sample loss during collection (if any) can be monitored. The process is compatible with sample liquefaction at room temperature. The exemplary device and method allows the sample to accumulate to the bottom of the reservoir as it liquefies. The exemplary device and method allows recording of sample volume after liquefaction. The exemplary device and method allows mixing of sperm rich fractions with seminal plasma for subsequent SPERMEOGRAM and/or SPERMCHECK analyses. The exemplary device and method allows samples to be harvested directly from the storage reservoir by pipette or swab. The exemplary device and method may be used in hospitals, clinics, labs and home for sample collection and liquefaction of the ejaculated semen. The exemplary device and method may also be used to safely transfer postcoital semen collected in a condom by puncturing or cutting the tip of the condom and expressing the semen into the collecting chamber for subsequent semen liquefaction and analyses. The exemplary device provides a sterile single piece device does not require any scissors, funnel, condom, or tube unlike other semen collection systems such as the Hygene Collection Kit. The exemplary device and method may be compatible with semen collection by coitus interruption or masturbation. Alternatively, it is feasible that a port (not shown) is provided on the reservoir to allow for drainage or other access or communication to the collected sample.

Example No. 2

Referring to FIG. 9, the exemplary embodiments is a glans compatible, sterilizable, single semen ejaculation device 11 may be made of soft transparent polyethylene or similar material. The collection device 11 has a glans accommodating collecting portion 19 that may have about a two inch diameter rim 15 that defines an opening 16 that tapers down to about a one inch diameter reservoir 21 to collect and measure the ejaculated semen (these dimensions are intended to be exemplary and not limiting. Other dimensions may be implemented as desired or required.). The height of the glans accommodating portion 21 may be about 1.5 inch (This dimension is intended to be exemplary and not limiting. Other dimensions and contour shapes may be implemented as desired or required). The chamber 13 also has a frosted surface or means 53 for labeling or tracking the collector's name, collection time, period of abstinence and semen volume. The semen storage reservoir 21 which is about 1.0 inch in diameter, about 1.5 inch in height and graduated in milliliters, for example, to determine sample volumes between ≦1.0 ml to 10.0 ml (These dimensions and volumes are intended to be exemplary and not limiting. Other dimensions and volumes may be implemented as desired or required.).

The entire device 11 stands on a flat surface by virtue of support from the skirt, such legs 25 or collars 27, for example, which may at least partially surrounds the entire height of the unit. The height of the skirt is about three inches (This dimension is intended to be exemplary and not limiting. Other dimensions may be implemented as desired or required.). A rim 24 projects at the bottom of the skirt by about 3/16 of an inch to provide additional support for standing (this dimension is intended to be exemplary and not limiting. Other dimensions may be implemented as desired or required.). The entire unit 12, or at least a partially, may remain in a sterile packet before use for safe semen evaluation practice and use in IVF/ICSI clinics, hospitals, laboratories, and research centers, or the like.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, material, dimension, time period, or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A human glans penis accommodating device for collecting all fractions of ejaculated semen sample received from the glans penis after masturbation and/or post coital interruption, said device comprising:
    a chamber, said chamber comprising a distal end, a proximal end, and a conduit extending between said distal end and proximal end;
    said proximal end having a rim defining an aperture;
    said distal end having a surface that encloses said conduit;
    at least a portion of said conduit proximal to said proximal end having a tapered shape radially inward defining a tapered section, whereby said tapered section accommodates the head of the glans penis;
    at least a portion of said conduit proximal to said distal end adapted for receiving the semen ejaculated from the glans penis, said receiving portion defining a reservoir section for the semen; and wherein:
        said tapered accommodation section is configured to prevent loss of any fractions of semen during ejaculation;
        said reservoir section is configured to prevent loss of any fractions of semen during ejaculation; and
        wherein said tapered accommodation section and said reservoir section are attachable to one another and/or detachable from one another.

2. The device of claim 1, wherein said tapered accommodation section is configured to the general external image of the head of the glans penis.

3. The device of claim 1, wherein said enclosure surface is adapted to allow said chamber to stand upward on a surface.

4. The device of claim 1, wherein said enclosure surface is at least substantially flat to allow said device to stand upward on a flat surface.

5. The device of claim 1, wherein the longest cross-section of said reservoir section is equal to or less than the shortest cross-section of the tapered accommodation section.

6. The device of claim 5, wherein said enclosure surface is adapted to allow said chamber to stand upward on a surface.

7. The device of claim 6, wherein said enclosure surface is at least substantially flat to allow said device to stand upward on a flat surface.

8. The device of claim 1, wherein the longest cross-section of said reservoir section is greater than the shortest cross-section of the tapered accommodation section.

9. The device of claim 8, wherein said enclosure surface is adapted to allow said chamber to stand upward on a surface.

10. The device of claim 9, wherein said enclosure surface is at least substantially flat.

11. The device of claim 1, further comprising:
    at least one protruding member disposed on said chamber, said protruding member adapted to allow said chamber to stand upward on a surface.

12. The device of claim 11, wherein said protruding member comprises at least one leg.

13. The device of claim 11, wherein said protruding member comprises a collar surrounding at least a portion of said chamber.

14. The device of claim 11, wherein the longest cross-section of said reservoir section is equal to or less than the shortest cross-section of the tapered accommodation section.

15. The device of claim 11, wherein the longest cross-section of said reservoir section is greater than the shortest cross-section of the tapered accommodation section.

16. The device of claim 1, wherein said tapered accommodation section is bell-shaped.

17. The device of claim 1, wherein said tapered accommodation section is olive-shaped.

18. The device of claim 1, wherein said tapered accommodation section is hemispherical-shaped.

19. The device of claim 1, wherein said tapered accommodation section is ellipsoid-shaped.

20. The device of claim 1, wherein said tapered accommodation section is multifaceted-shaped.

21. The device of claim 1, wherein said tapered accommodation section is cone-shaped.

22. The device of claim 1, wherein said tapered accommodation section comprises at least one wall, wherein said at least one wall comprises a shape selected from the group consisting of curved, multicurved, sloped, multifaceted, beveled, sloped, and chamfered.

23. The device of claim 1, further comprising a cover disposed on said chamber.

24. The device of claim 1, further comprising a cover disposed on said device.

25. The device of claim 1, further comprising a tracking medium disposed on said chamber.

26. The device of claim 25, wherein said a tracking medium comprises at least one of frosted surface or bar code label.

27. The device of claim 1, further comprising a volume identification medium disposed on said chamber.

28. The device of claim 27, wherein said a volume identification medium comprises at least one graduated mark or a calibrated region adapted for indicating volume.

29. The device of claim 1, wherein said device is used for an application selected from the group consisting of hospitals, clinics, semen analysis laboratories, fertility and infertility diagnostic laboratories, IVF clinics, ICSI clinics, artificial insemination clinics, vasectomy clinics, andrology research laboratories, basic research laboratories, forensic (crime) laboratories and law enforcement agencies, prisons, home sperm test users, and environmental monitoring for effect of toxins on spermatogenesis in occupations such as mining, agriculture, radiation exposure, and industries.

30. The device of claim 1, further comprising a port disposed on said reservoir section to allow for drainage or removal of the semen.

31. The device of claim 1, further comprising a port disposed on said reservoir section to allow for access or communication to the semen.

32. The device of claim 1, wherein said chamber is partially integrally formed.

33. The device of claim 1, wherein said device is partially integrally formed.

34. The device of claim 1, further comprising an adapter section.

35. The device of claim 34, further comprising at least one handle disposed on said device.

36. The device of claim 35, wherein said handle comprise at least one of tab, ridge, strap, knob, protrusion, or lever.

37. The device of claim 34, further comprising at least one grip ridge disposed on said device.

38. The device of claim 34, wherein said adapter section comprises a collar.

39. The device of claim 38, wherein said adapter section is configured to accommodate the glans penis.

40. The device of claim 38, wherein said collar comprises at least one of lubricant, jacket or lining.

41. The device of claim 34, wherein said adapter section comprises an ejaculation aid device.

42. The device of claim 34, wherein said adapter section comprises a stimulation device for stimulating the glans.

43. The device of claim 34, wherein said adapter section is adapted for being held by the individual or a partner.

44. The device of claim 1, wherein said reservoir section at least partially comprises at least one communication channel.

45. The device of claim 44, wherein said at least one communication channel comprises at least one of channel, microchannel, capillary tube, microtubing, tubing, pipette, micropipette, or column.

46. The device of claim 1, further comprising a port disposed on said collection device.

47. The device of claim 46, wherein said port is in communication with at least one communication channel.

48. The device of claim 47, wherein said at least one communication channel comprises at least one of channel, microchannel, capillary tube, microtubing, tubing, pipette, micropipette or column.

49. The device of claim 1, further comprising at least one handle disposed on said device.

50. The device of claim 49, wherein said handle comprise at least one of tab, ridge, strap, knob, protrusion, or lever.

51. The device of claim 1, further comprising at least one grip ridge disposed on said device.

52. The device of claim 1, further comprising a port disposed on said collection device.

53. The device of claim 1, further comprising a base in communication with said device, said base adapted to allow said chamber to stand upward on a surface.

54. The device of claim 43, wherein said communication comprises a connector.

55. The device of claim 54, wherein said connector comprises at least one leg or stem.

56. The device of claim 54, wherein said connector comprises a joining or adhesive means.

* * * * *